United States Patent [19]
Napolitano et al.

[11] Patent Number: 5,496,558
[45] Date of Patent: Mar. 5, 1996

[54] SOLID FORM XEROSTOMIA PRODUCT

[75] Inventors: Neil J. Napolitano, Fanwood; Kuo-Chen Yeh, Westfield, both of N.J.; Frank J. Sena, Brooklyn, N.Y.; Phil J. Oths, Mendham; Manuel M. Roque, Nutley, both of N.J.

[73] Assignee: Block Drug Company Inc., Jersey City, N.J.

[21] Appl. No.: 25,174

[22] Filed: Mar. 2, 1993

[51] Int. Cl.$^6$ .............................. A61F 13/00; A61K 9/20
[52] U.S. Cl. .............................. 424/435; 424/55; 424/465
[58] Field of Search ..................................... 424/423, 434, 424/435, 55, 465

[56] References Cited

U.S. PATENT DOCUMENTS

| | | | |
|---|---|---|---|
| 4,820,506 | 4/1989 | Kleinberg et al. | 424/40 |
| 4,938,963 | 7/1990 | Parnell | 424/440 |
| 5,135,752 | 8/1992 | Snipes et al. | 424/435 |
| 5,143,731 | 9/1992 | Viegas et al. | 424/435 |
| 5,147,648 | 9/1992 | Bannert | 424/434 |
| 5,156,845 | 10/1992 | Grodberg | 424/440 |
| 5,244,668 | 9/1993 | Snipes et al. | 424/435 |

FOREIGN PATENT DOCUMENTS 2159052 11/1985 United Kingdom.
9109609 7/1991 WIPO.

*Primary Examiner*—Peter F. Kulkosky
*Attorney, Agent, or Firm*—Ostrolenk, Faber, Gerb & Soffen

[57] ABSTRACT

A solid dosage form for relieving xerostomia symptoms comprising a lubricating polymer comprising polyethylene oxide and a sialogogue in a pharmaceutically acceptable, substantially non-cariogenic, carrier.

12 Claims, No Drawings

SOLID FORM XEROSTOMIA PRODUCT

BACKGROUND OF THE INVENTION

Xerostomia (dry mouth syndrome) is the result of compromised salivary flow and is associated with a wide variety of conditions and causative agents. The condition can be the result of a pathological state such as Sicca Syndrome (Sjogren's disease), dry gland disease, polyglandular failure disfunction, and the like. According to a 1986 National Institute of Dental Research publication, over 300 commonly used drugs listed dry mouth as a side effect of their use, the most prevalent of which were the hypertensives and anti-depressants, while others included pain killers, tranquilizers, diuretics and even over-the-counter antihistamines. In addition, treatments such as radiation treatment for tumors in the head and neck region can cause the sensation of dry mouth. Furthermore, age and stress have been linked to xerostomia.

The compromised salivary flow is frequently responsible for a variety of symptoms such as a burning sensation in the mouth, difficulty with speech, eating and tasting, and the like. It can lead to mucosal infections, bacterial sialadentis, periodontal disease and dental caries.

Dry mouth sufferers have used a variety of self-help treatments, but these have not been particularly satisfactory. Liquid remedies such as water and artificial saliva offer short lived help, and the artificial saliva exhibits a consistency similar to natural saliva which some sufferers view as distasteful. Solid aids such as citric rinds and hard candies are damaging to tooth enamel and extend no lubricating comfort.

A Jaboradini derivative, pilocarpine, has been used as a sialogogue drug with success. However, the drug is a muscarinic agonist which is known to produce such non-specific systemic side effects as excessive tearing and runny noses. The drug also presents the danger of cardiac arrest if misused.

Numerous are the approaches which have been taken to soothe dry mouth discomfort appear in the literature. Some, like those described in U.S. Pat. No. 4,088,788 use masticatory stimulation to induce salivation and some like in U.S. Pat. No. 4,400,372 use an acid containing chewing gum to achieve both masticatory and gustatory stimulation. U.S. Pat. No. 5,156,845 teaches a lozenge with an acidulate, employing gustatory stimulation to relieve oral dryness and also includes a fluoride source to promote remineralization of the teeth. U.S. Pat. No. 4,265,877 describes a chewing gum which includes a fluoride source for the same purpose.

Hutchinson describes the development of artificial saliva tablets in New Zealand Pharmacy, 7:30, 1987. He had been using an artificial saliva but characterized it as a "better-than-nothing" approach. The reason was that it supported mold growth after a short time, the relief achieved was temporary unless the fluid was continuously applied, which meant considerable social inconvenience, and the sorbitol used in the product caused irritation and painful sensations of the tongue and mucosa. Noting that polyethylene oxide as a 2% solution had been used with advantage, Hutchinson proceeded to prepare tablets which when slowly sucked, taking sips of water, dissolved in the mouth, coating the mucosa and relieving systems of xerostomia. Formulations containing polyethylene oxide alone or 70–90% polyethylene oxide combined with citric acid (with or without flavoring and sweetener) were prepared. After "some disastrous results" the citric acid was eliminated as it appeared to be inhibiting the tableting flow properties, possibly due to uptake of water from the atmosphere.

While Hutchinson apparently noted no advantage to the citric acid and abandoned its use due to formulation difficulties, it has now been discovered that a highly advantageous product for the relief of the symptoms of xerostomia can be achieved by employing both polyethylene oxide and citric acid, if appropriately formulated.

It is accordingly the object of the invention to provide a novel composition which is advantageous for relief of the symptoms of xerostomia. This and other objects of the advantage will become apparent to those of ordinary skill in the art of formulation from the following detailed description.

SUMMARY OF THE INVENTION

This invention relates to a solid dosage form product for the relief of the symptoms of xerostomia. More particularly, it relates to a solid dosage form product which contains a lubricating polymer comprising polyethylene oxide and a sialogogue in a pharmaceutically acceptable, substantially non-cariogenic carrier.

DETAILED DESCRIPTION OF THE INVENTION

In accordance with the present invention, a solid dosage form product for the relief of xerostomia is provided. The solid dosage form can be a lozenge, tablet, chewing gum, pastille or the like and contains three principle ingredients which are a lubricating polymer comprising polyethylene oxide, a sialogogue and a pharmaceutically acceptable, substantially non-cariogenic carrier. The composition preferably also contains a source of mineral ions and a source of fluoride.

Any known carrier material or composition which is either not cariogenic or low-cariogenic, i.e., is substantially non-cariogenic, can be used in the product of this invention. Thus, carrier materials which have heretofore been used in lozenges, chewing gums, pastilles, hard candy and the like can be employed. Examples of non- or low-cariogenic polyols which can be used include mannitol, galactitol, isomaltose, and the like. The preferred carrier is constituted by about 10 to 100% sorbitol, preferably about 40–98% and most preferably about 80–97%, in combination with xylitol in an amount from 0–90%, preferably 2–60% and most preferably about 3–20%. The carrier constitutes about 20–99% of the oral solid dosage form and preferably about 85–98%.

The sialogogue used in the present invention is a pharmaceutically acceptable organic acid which can reduce the oral pH sufficiently to cause demineralization of the teeth. Examples include citric acid, malic acid, ascorbic acid, fumaric acid, and the like. Citric acid is the preferred agent. The sialogogue is generally present in an amount of about 0.1 to 2% of the composition and preferably about 0.2 to 1.5%. As a result, the composition of this invention will have a pH, when measured in the form of a 50% aqueous solution, of about 3 to 5.

The composition of this invention also contains a lubricating polymer in an amount from about 0.001 to 50% and preferably 0.01 to 5%. The lubricating polymer includes polyethylene oxide (PEO) which generally has a molecular weight of about 8,000 to 4,000,000, preferably about 200,000 to 4,000,000. The polyethylene oxide may be used alone or in combination with other lubricating polymers such as mucins, cellulose gums and polycarbophil. When present, the other polymers will constitute up to about 5% of the composition and preferably up to about 2%. The polyethylene oxide is uniquely suited to use in the mouth because of its considerable lubrication properties and its ability to form association compounds with mucins, the class of glycoprotein which provides lubrication in natural saliva.

Because the composition tends to demineralize the teeth, it preferably contains a source of mineral ions and a source of fluoride. The mineral ions are those normally found in saliva and include sodium, potassium, calcium, magnesium, and phosphate. The mineral source is generally present in an amount of about 0.1 to 15%, preferably about 0.3 to 10%. The fluoride is normally present in an amount of 0.1–100 ppm, preferably about 1–5 ppm. The composition can also include other ingredients normally found in solid dosage form materials, such as flavoring, coloring, and the like.

A clinical test was conducted to evaluate the efficacy of various dry mouth products. In the first phase, five oral rinses, a lozenge and two types of chewing gums were compared. Participants were asked to provide a rating on a 9 point scale at the inception of the test and for the tested material after one week of use. Results were averaged and it was found that the lozenge form was the most preferred. Part of the results are shown in Table 1 below which compared a commercially available oral rinse containing a cellulose gum with a lozenge which contained citric acid, commercially available porcine mucin and polyethylene oxide.

TABLE 1

| Question | Oral Rinse | | | Lozenge | | |
|---|---|---|---|---|---|---|
| | Base-line | Week | % Change | Base-line | Week | % Change |
| Dryness | 4.91 | 5.73 | +16.1 | 4.44 | 5.84 | +31.5 |
| Eating | 5.76 | 5.91 | +2.6 | 6.32 | 6.60 | +4.4 |
| Talking | 5.76 | 6.36 | +10.4 | 5.80 | 6.32 | +9.0 |
| Average | 5.48 | 6.00 | +9.7 | 5.52 | 6.25 | +15.0 |

The lozenge had almost twice the degree of improvement in subject-perceived dryness (31.5% v. 16.1%) and overall, the combined improvement scores in the three critical variables (dryness, difficulty in eating, and difficulty in talking) was 15% for the lozenge and only 9.7% for the oral rinse. The lozenge taste was generally considered "moderately pleasant" while the oral rinse was rated as "neutral" (7.6 v. 5.0 on the 9 point scale).

Seven different lozenge compositions and one gel composition were then tested. A lozenge containing citric acid and polyethylene oxide was found to be more effective at relieving the symptoms of xerostomia than a lozenge which contains citric acid alone. This is shown in Table 2 below.

TABLE 2

| Question | Citric Acid Alone | | | Citric Acid and PEO | | |
|---|---|---|---|---|---|---|
| | Base-line | Week | % Change | Base-line | Week | % Change |
| Dryness | 5.30 | 5.50 | +3.8 | 4.80 | 5.40 | +12.5 |
| Eating | 5.40 | 5.90 | +9.3 | 5.40 | 6.30 | +16.7 |
| Talking | 6.30 | 6.40 | +1.6 | 5.80 | 6.40 | +10.3 |
| Bothered | 5.50 | 5.70 | +3.6 | 5.10 | 5.70 | +11.8 |
| Average | 5.63 | 5.88 | +4.6 | 5.28 | 5.95 | +12.8 |

Overall, the combined percent improvement in the four critical variables (dryness, difficulty in eating, difficulty in talking and extent to which dryness was bothersome) was 12.8 for the citric acid/polyethylene oxide lozenge and only 4.6 for the lozenge with citric acid only. In addition, the lozenge with both agents was found to be better at stimulating salivary flow than the lozenge with citric acid only. This is shown in Table 3 below.

TABLE 3

| Comparison of Salivery Flow Rates | | | | |
|---|---|---|---|---|
| | | | Stimulated | |
| | Un-stimulated | Stimulated (2% Citric Acid Rinse) | Lozenge w/ citric acid | Lozenge w/ citric acid/PEO |
| Group 1 | 0.09 | 0.40 | 0.34 | — |
| (% change) | | (+344%) | (+277%) | — |
| Group 2 | 0.11 | 0.49 | — | 0.57 |
| (% change) | | (+345%) | — | (+418%) |

In this table, flow rates are in mL/min based on the sum of the parotid and half the submandibular/sublingual flow rates. Percent change is from unstimulated flow.

The lozenge containing only citric acid more than doubled the mean combined salivary flow, but the addition of polyethylene oxide increased the flow by more than a factor of four.

An in vitro demineralization/remineralization study was performed to establish a safety profile for the product with respect to tooth enamel. A pH cycling protocol was established in which an enamel specimen was immersed in a demineralizing acetate solution for about 6 hours followed by immersion in the test product (in 50% solution form) for 5 to 15 minutes and then in a mineralizing solution for about 17 hours, sequentially, for a 14 day period. The enamel was then examined by cross-sectional microhardness examination at two "window" depths and a companion study using scanning electron micrographs was performed. A 0.05% sodium fluoride rinse was used as a control and no marked demineralization was noted. A lozenge without the mineral components was noted to be demineralizing while commercial candies which were sorbitol based were also noted to be demineralizing. A lozenge containing polyethylene oxide and citric acid and minerals was observed to provide substantially less demineralization than the other lozenge. The test performed was tailored to fluoride rinses and dentifrice treatment which contain about 100 times more fluoride than in the lozenge of the instant invention. It was not possible to overcome the severe damage caused by the acetate with a product containing fluoride in parts per million range other than in the present invention. Nevertheless, the mineral containing lozenge of the invention appeared to provide sufficient protection to balance the detrimental effect of the demineralizing agent. The scanning electron micrographs provided obvious visual confirmation of the superiority of the experimental lozenges with fluoride, calcium and phosphate.

Lozenges were prepared following the general procedures used in hard candy manufacture. A commercial available sorbitol solution with or without xylitol and the mineral source, including the fluoride source, were heated to about 160° C. under ambient or vacuum conditions. The molten mass was cooled to about 125° C. and citric acid added while mixing. At 105° C., the lubricating polymer(s) is slurried in an aliquot of the sorbitol solution and added while mixing the molten mass. The mass is allowed to cool and when the temperature is in the range of 80°–90° C., flavor and a seed sorbitol powder having a particle size customary for the nucleation of amorphous crystalline sorbitol is added in an amount of about 0.01–1%, preferably 0.1–0.5%. The resulting molten mixture is placed into molds while the temperature is in the range of 75°–90° C., and allowed to harden for 30 minutes to 5 hours, depending on variables including the lozenge composition, size (typically 0.5–5 grams each) and type of mold. Lozenge formulations according to the present invention prepared are set forth in Examples 1 through 4 below.

EXAMPLE 1

|  | % (wt/wt) |
| --- | --- |
| Minerals (including 2 ppm fluoride) | 0.9 |
| PEO (4,000,000 MW) | 0.7 |
| Citric acid | 0.7 |
| Water | 2.5 |
| Flavor, color | 0.3 |
| Sorbitol solution | Q.S. to 100 |

EXAMPLE 2

|  | % (wt/wt) |
| --- | --- |
| Hydrogenated starch hydrolysate | 20.0 |
| Minerals (including 1 ppm fluoride) | 0.9 |
| PEO (200,000 MW) | 1.5 |
| Malic acid | 0.5 |
| Water | 2.0 |
| Flavor, color | 0.2 |
| Sorbitol solution | Q.S. to 100 |

EXAMPLE 3

|  | % (wt/wt) |
| --- | --- |
| Minerals (including 5 ppm fluoride) | 0.9 |
| Polyethylene oxide (600,000 MW) | 0.7 |
| Ascorbic acid | 0.3 |
| Citric acid | 1.0 |
| Water | 2.5 |
| Flavor, color | 0.4 |
| Xylitol | 10.0 |
| Sorbitol solution | Q.S. to 100 |

EXAMPLE 4

|  | % (wt/wt) |
| --- | --- |
| Minerals (including 3 ppm fluoride) | 0.9 |
| PEO: (4,000,000 MW) | 0.7 |
| (9,000 MW) | 30.0 |
| Fumaric acid | 0.2 |
| Water | 3.0 |
| Flavor, color | 0.4 |
| Xylitol | 30.0 |
| Mucin MX (Porcine, in xylitol) | 1.5 |
| Sorbitol solution | Q.S. to 100 |

EXAMPLE 5

A tablet was produced by compressing the mixture set forth below at a compression force of about 20 kilo Newtons.

|  | % (wt/wt) |
| --- | --- |
| Mixed Dextrins | 42.0 |
| Minerals (including 4 ppm fluoride) | 0.2 |
| Citric acid | 2.0 |
| Flavor, color | 0.2 |
| Talc | 0.9 |
| PEO: (4,000,000 MW) | 0.5 |
| (200,000 MW) | 0.1 |
| Sorbitol | Q.S. to 100 |

EXAMPLE 6

To form a chewing gum, the following ingredients were admixed at elevated temperatures:

|  | % (wt/wt) |
| --- | --- |
| Chewing gum base (Dreyfus) | 24.0 |
| Hydrogenated starch hydrolysate | 11.5 |
| Mucin MS (porcine, in xylitol) | 6.0 |
| Water | 1.9 |
| Flavor, color | 0.4 |
| Glycerin | 1.0 |
| Encapsulated citric acid | 0.5 |
| PEO: (4,000,000 MW) | 0.5 |
| (600,000 MW) | 0.1 |
| Lecithin | 0.4 |
| Citric Acid powder | 0.4 |
| Minerals (including 1 ppm fluoride) | 0.3 |
| Calcium saccharin | 0.1 |
| Sorbitol | Q.S. to 100 |

EXAMPLE 7

A pastille was prepared by heating the composition set forth below and allowing evaporation until a desired moisture content followed by folding in molten xylitol (350 grams). The resulting mixture was deposited in a mold and allowed to undergo further evaporation to form a firm, jelly-like consistency product.

|  | % (wt/wt) |
| --- | --- |
| Gelatin | 100 |
| Hydrogenated Glucose syrup | 500 |
| Xylitol | 350 |
| Citric acid | 35 |
| Minerals (including 1 ppm fluoride) | 90 |
| PEO: (600,000 MW) | 12 |
| Flavor, color | 3 |
| Water | 215 |

Although the present invention has been described in relation to particular embodiments thereof, many other variations and modifications will become apparent to those skilled in the art. The disclosed embodiments were intended to be illustrative only and were not intended to be limiting. In the above examples, as throughout this specification and claims, all parts and percentages are by weight and all temperatures are in degrees Centigrade, unless otherwise indicated.

What is claimed is:

1. A solid product for relieving xerostomia symptoms which comprises a lubricating polymer comprising a polyethylene oxide having a molecular weight of 8,000 to 4,000,000 in an amount of about 0.01–5%, a pharmaceutically acceptable organic acid sialogogue in an amount of about 0.1–2%, and a sorbitol containing carrier in an amount of 20–99%, said sorbitol containing carrier containing about 10 to 100% sorbitol.

2. A product according to claim 1 in which the pharmaceutically acceptable organic acid sialogogue is selected from the group consisting of citric acid, malic acid, ascorbic acid and fumaric acid, and said sorbitol containing carrier contains about 40–98% sorbitol.

3. A product according to claim 2 in which the lubricating polymer comprises polyethylene oxide in admixture with mucin, polycarbophil or cellulose gum.

4. A product according to claim 2 which includes a source of mineral ions and a source of fluoride.

5. A product according to claim 4 in which the sialologue is present in an amount of 0.1–2%, the source of mineral ions is present in an amount of 0.1–15%, the fluoride is present in an amount of 0.1–100 ppm and the carrier is present in an amount of 20–99%.

6. A product according to claim 2 in which the carrier comprises 40–98% sorbitol in combination with up to 60% xylitol.

7. A product according to claim 6 in which the lubricating polymer comprises polyethylene oxide in admixture with mucin, polycarbophil or cellulose gum.

8. A product according to claim 7 which includes a source of mineral ions and a source of fluoride.

9. A product according to claim 8 in which the sialologue is present in an amount of 0.1–2%, the lubricating polymer is present in an amount of 0.001–50%, the source of mineral ions is present in an amount of 0.1–15%, the fluoride is present in an amount of 0.1–100 ppm and the carrier is present in an amount of 20–99%.

10. A composition according to claim 8 in which the sialologue is present in an amount of 0.2–1.5%, the lubricating polymer is present in an amount of 0.01–5%, the source of mineral ions is present in an amount of 0.1–10%, the fluoride is present in an amount of 1–5 ppm and the carrier is present in an amount of 85–98%.

11. A product according to claim 1 in the form of a lozenge or chewing gum.

12. A product according to claim 2 in the form of a lozenge or chewing gum.

* * * * *